(12) United States Patent
Ivinson et al.

(10) Patent No.: US 10,279,146 B2
(45) Date of Patent: May 7, 2019

(54) CANNULATED DISPOSABLE TORQUE LIMITING DEVICE WITH PLASTIC SHAFT

(71) Applicant: ECA Medical Instruments, Newbury Park, CA (US)

(72) Inventors: David Ivinson, Camarillo, CA (US); John Nino, Simi Valley, CA (US)

(73) Assignee: ECA MEDICAL INSTRUMENTS, Thousand Oaks, CA (US)

( * ) Notice: Subject to any disclaimer, the term of this patent is extended or adjusted under 35 U.S.C. 154(b) by 654 days.

(21) Appl. No.: 14/728,945

(22) Filed: Jun. 2, 2015

(65) Prior Publication Data
US 2016/0354581 A1 Dec. 8, 2016

(51) Int. Cl.
*A61B 17/00* (2006.01)
*A61B 17/88* (2006.01)
(Continued)

(52) U.S. Cl.
CPC ..... *A61M 25/0113* (2013.01); *A61B 17/8875* (2013.01); *B25B 23/141* (2013.01); *B25B 23/1422* (2013.01); *B25B 23/1427* (2013.01); *B25B 23/18* (2013.01); *A61B 17/00491* (2013.01); *A61B 2090/031* (2016.02); *F16B 29/00* (2013.01); *F16B 37/002* (2013.01); *F16B 37/005* (2013.01); *Y10T 403/4949* (2015.01);
(Continued)

(58) Field of Classification Search
CPC ......... Y10T 403/4949; Y10T 403/4958; Y10T 403/4966; F16B 29/00; F16B 37/002; F16B 37/005; A61M 25/0113; B25B 23/1422

See application file for complete search history.

(56) References Cited

U.S. PATENT DOCUMENTS 3,003,378 A 10/1961 Hotchner
3,168,944 A 2/1965 Zimmerman
(Continued)

FOREIGN PATENT DOCUMENTS

CN 2238511 Y 10/1996
CN 1138511 A 12/1996
(Continued)

OTHER PUBLICATIONS

International Patent Application No. PCT/US2011/034607; Int'l Search Report; dated Feb. 8, 2012; 3 pages.
(Continued)

*Primary Examiner* — Ellen C Hammond
(74) *Attorney, Agent, or Firm* — BakerHostetler (57) ABSTRACT

A torque-limiting device may include a shaft extending axially through upper and lower shanks, a spring, and a nut to an end opening of a handle. The upper and lower shanks may be under a force from the spring and further configured to selectively engage within a predetermined torque limit and disengage at above the predetermined torque limit. Accordingly, the shaft may receive torque up to the predetermined limit as provided by a user operating a handle of the torque-limiting device. The torque-limiting device may be disposable, reusable, economical, and have high torque capabilities. The shaft may be of a plastic material and include a lumen extending there through, and through which a variety of devices and materials may be delivered to a workpiece.

29 Claims, 11 Drawing Sheets

(51) Int. Cl.
  A61B 90/00 (2016.01)
  A61M 25/01 (2006.01)
  B25B 23/14 (2006.01)
  B25B 23/18 (2006.01)
  B25B 23/142 (2006.01)
  F16B 29/00 (2006.01)
  F16B 37/00 (2006.01)

(52) U.S. Cl.
  CPC .... *Y10T 403/4958* (2015.01); *Y10T 403/4966* (2015.01)

(56) References Cited

U.S. PATENT DOCUMENTS

| | | | |
|---|---|---|---|
| 3,354,754 | A | 11/1967 | Amtsberg et al. |
| 3,557,655 | A * | 1/1971 | Coe ...................... F16B 37/002 411/436 |
| 3,600,014 | A * | 8/1971 | Harris ................... F16G 11/048 174/176 |
| 3,695,059 | A | 10/1972 | Laubach |
| 4,883,130 | A | 11/1989 | Dixon |
| 5,501,124 | A | 3/1996 | Ashby |
| 5,501,541 | A * | 3/1996 | Gomes ................... A47C 4/022 403/19 |
| 5,576,501 | A | 11/1996 | Huang |
| 5,931,062 | A | 8/1999 | Marcovici |
| 6,128,984 | A | 10/2000 | Haupt |
| 6,189,666 | B1 | 2/2001 | Willmot |
| 6,439,086 | B1 | 8/2002 | Bahr |
| 7,181,997 | B1 | 2/2007 | Rinner et al. |
| 7,197,968 | B2 | 4/2007 | Bubel |
| D543,433 | S | 5/2007 | Gao |
| 7,243,581 | B1 | 7/2007 | Gao |
| D557,584 | S | 12/2007 | Gao |
| D562,665 | S | 2/2008 | Gao |
| 7,334,509 | B1 | 2/2008 | Gao |
| 7,389,700 | B2 | 6/2008 | Gao |
| 7,395,738 | B1 | 7/2008 | Nelson |
| 7,434,623 | B2 | 10/2008 | Von Gynz-Rekowski |
| D580,730 | S | 11/2008 | Gao |
| 7,467,576 | B2 | 12/2008 | Gao |
| 7,475,619 | B2 | 1/2009 | Chiu et al. |
| 7,516,676 | B2 | 4/2009 | Gao |
| 7,650,821 | B2 | 1/2010 | Gauthier et al. |
| 7,740,249 | B1 | 6/2010 | Gao |
| 7,762,164 | B2 | 7/2010 | Nino et al. |
| 7,793,573 | B2 | 9/2010 | Gao |
| 7,806,027 | B1 | 10/2010 | Gao |
| 7,810,817 | B1 | 10/2010 | Gao |
| 7,938,046 | B2 | 5/2011 | Nino et al. |
| 7,992,472 | B2 | 8/2011 | Gao |
| 8,758,413 | B2 | 6/2014 | Heiges et al. |
| 2004/0115014 | A1 | 6/2004 | Totsu |
| 2006/0016300 | A1 | 1/2006 | Bubel |
| 2006/0120822 | A1 * | 6/2006 | Kaye ...................... F16B 13/001 411/30 |
| 2006/0179981 | A1 | 8/2006 | Cutler et al. |
| 2006/0248988 | A1 | 11/2006 | Bennett |
| 2006/0278051 | A1 | 12/2006 | Gauthier et al. |
| 2007/0289391 | A1 | 12/2007 | Gao |
| 2009/0187216 | A1 * | 7/2009 | Schmieding ....... A61B 17/0401 606/232 |
| 2009/0194307 | A1 | 8/2009 | Rinner |
| 2009/0248029 | A1 * | 10/2009 | Paulos ............... A61B 17/8645 606/104 |
| 2009/0248035 | A1 | 10/2009 | Johan |
| 2009/0255386 | A1 | 10/2009 | Liao |
| 2009/0260490 | A1 | 10/2009 | Cutler et al. |
| 2009/0293687 | A1 | 12/2009 | Nino et al. |
| 2010/0057137 | A1 | 3/2010 | Heiges et al. |
| 2010/0275744 | A1 | 11/2010 | Wengreen et al. |
| 2011/0000347 | A1 | 1/2011 | Stark |
| 2011/0184425 | A1 | 7/2011 | Cheraux |
| 2013/0276597 | A1 | 10/2013 | Ivinson et al. |
| 2013/0276598 | A1 | 10/2013 | Ivinson et al. |
| 2013/0319190 | A1 * | 12/2013 | Nino ...................... B25B 23/141 81/475 |
| 2014/0137710 | A1 | 5/2014 | Hsieh |
| 2016/0153489 | A1 * | 6/2016 | Pollitt ................... B29C 53/585 403/343 |

FOREIGN PATENT DOCUMENTS

| | | |
|---|---|---|
| CN | 1505555 A | 6/2004 |
| EP | 0724934 A1 | 8/1996 |
| JP | 2001-121444 | 5/2001 |
| JP | 2007-068970 A | 3/2007 |
| WO | WO 1992/003262 A1 | 3/1992 |
| WO | WO 2005/077603 A1 | 8/2005 |
| WO | WO 2008/075186 A2 | 6/2008 |
| WO | WO 2011/139902 A2 | 11/2011 |

OTHER PUBLICATIONS

International Patent Application No. PCT/US2011/034618; Int'l Search Report and the Written Opinion; dated Feb. 17, 2012; 8 pages.
Chinese Office Action dated Sep. 4, 2014, issued in Chinese Patent Application No. 201180033625.2; 13 pages.
International Patent Application No. PCT/US2011/044840; Int'l Search Report and the Written Opinion; dated Feb. 23, 2012; 8 pages.
Holmed Corporation Surgical Instruments Catalog; www.holmed.net; Precision Engineered Products LLC; 2014; accessed Jun. 25, 2015; 1 page.
Beere Medical Line of Custom Configured Ortho-Grip Handles; www:teleflexmedicaloem.com; accessed Jun. 25, 2015; 2 pages.
Bradshaw Medical, Inc.,; Non-Ratcheting and Fixed Comfort Grip Handles; www.bradshaw-medical.com; 2015; accessed Jun. 25, 2015; 2 pages.
Paragon Medical Standard Surgical Instrumentation Catalog; www.paragonmedical.com/catalog/complete-catalog.html; accessed Jun. 25, 2015; 8 pages.
Quick Connectors & Adaptors, Gauthier Biomedical, Inc.; www.gauthierbiomedical.com/products/connects-adaptors; 2015; accessed Jun. 25, 2015; 2 pages.
Silicone Handles; Gauthier Biomedical, Inc.; www.gauthierbiomedical.com/products/silicone-handles; 2015; accessed Jun. 25, 2015; 2 pages.
Ratcheting Srewdrivers; Gauthier Biomedical Inc.; www.gauthierbiomedical.com/products/ratcheting-screwdrivers; 2015; accessed Jun. 25, 2015; 2 pages.
Torque Instruments, Gauthier Biomedical Inc.; www.gauthierbiomedical.com/products/torque-instruments; 2015; accessed Jun. 25, 2015; 1 page.
Symmetry Medical Inc.; Radel R Instrument Handles, Silicone Instrument Handles, Ratcheting Screwdriver Handles, and Spinal Instruments; www.symmetrymedical.com; 2015; accessed Jun. 25, 2015; 1 pages.
International Patent Application No. PCT/US2012/066234; Int'l Search Report and the Written Opinion; dated Feb. 21, 2013; 10 pages.

* cited by examiner

CANNULATED DISPOSABLE TORQUE LIMITING DEVICE WITH PLASTIC SHAFT

BACKGROUND

1. Field

This disclosure relates to a driver tool and, in particular, to a medical use torque-limiting driver that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

SUMMARY

Briefly stated, torque devices according to implementations of the present disclosure obviate the shortfalls of piecemeal systems by reducing the number of part-to-part transitions of torque.

According to aspects of one or more exemplary implementations, disclosed are torque-limiting drivers comprising a body having a handle comprising a lumen, an upper cylindrical shank, a lower cylindrical shank having a square drive socket, a nut, a spring between the upper cylindrical shank and the nut, wherein the spring is configured to apply a force across the upper cylindrical shank and the lower cylindrical shank, a shaft having a workpiece-engaging tip and a square drive connection engaged within the square drive socket of the lower cylindrical shank, wherein the shaft extends axially through the lower cylindrical shank, the upper cylindrical shank, the spring, and the handle with an end portion of the shaft disposed within the lumen of the handle, wherein the shaft has a plurality of thread rests on a portion of the shaft, wherein the thread rests are cut and engaged by a threading in the nut, wherein the shaft has a lumen extending across an axial length of the shaft, and wherein the shaft comprises a plastic material or a composite including plastic, wherein the upper cylindrical shank and the lower cylindrical shank engage for relative rotation, and wherein the upper cylindrical shank and the lower cylindrical shank disengage when a predetermined torque limit is exceeded.

The lumen may form a tube, and/or enclose a tube advanceable within said lumen. The lumen and/or tube may be configured to deliver a biologic material. The biologic material may be an adhesive. The biologic material may be a growth stimulant. The lumen is an enclosure through which a guidewire is advanceable. The drive socket may be a square drive socket and the drive connection may be a square drive connection. The shaft may be threadably engaged with the nut. A force provided by the spring may securely maintain the drive connection of the shaft engaged within the drive socket of the lower cylindrical shank. The nut may include a lower portion having an outer diameter substantially equal to an inner diameter of the spring and extending axially through at least a portion of the spring.

The torque-limiting driver may further comprise at least two washers between the spring and the upper cylindrical shank. The torque-limiting driver may further comprise a washer between the lower cylindrical shank and the body. The torque-limiting driver may further comprise a washer between the spring and the nut.

The upper cylindrical shank and the lower cylindrical shank may each have a plurality of teeth and an axial bore, the teeth having a vertical face, an inclined face and a substantially flat peak, wherein the inclined face is defined by a first radius of curvature that transitions to the substantially flat peak and wherein the teeth spiral around the axial bore. The vertical face may terminate in a second radius of curvature that transitions to the substantially flat peak and wherein the second radius of curvature is smaller than the first radius of curvature. The substantially flat surface may be wider at the outer radius than at the inner radius and wherein the substantially flat surface is perpendicular to the axis of the upper and lower shank. The transition from the first radius of curvature and second radius of curvature to the substantially flat peak may be smooth.

The predetermined torque limit may be at least 1 inch-ounce. The predetermined torque limit may be between about 16 inch-ounces and about 40 inch-ounces.

According to aspects of one or more exemplary implementations, disclosed are methods comprising providing to a workpiece a torque-limiting driver comprising a body having a handle comprising a lumen, an upper cylindrical shank, a lower cylindrical shank having a square drive socket, a nut, a spring between the upper cylindrical shank and the nut, wherein the spring is configured to apply a force across the upper cylindrical shank and the lower cylindrical shank, a shaft having a workpiece-engaging tip and a square drive connection engaged within the square drive socket of the lower cylindrical shank, wherein the shaft extends axially through the lower cylindrical shank, the upper cylindrical shank, the spring, and the handle with an end portion of the shaft disposed within the lumen of the handle, wherein the shaft has a plurality of thread rests on a portion of the shaft, wherein the thread rests are cut and engaged by a threading in the nut, wherein the shaft has a lumen extending across an axial length of the shaft, and wherein the shaft comprises a plastic material or a composite including plastic, wherein the upper cylindrical shank and the lower cylindrical shank engage for relative rotation, and wherein the upper cylindrical shank and the lower cylindrical shank disengage when a predetermined torque limit is exceeded, and the methods further comprising delivering a biologic material to the workpiece through the lumen.

The biologic material may be an adhesive. The biologic material may be a growth stimulant.

According to aspects of one or more exemplary implementations, disclosed are methods comprising providing to a workpiece a torque-limiting driver comprising a body having a handle comprising a lumen, an upper cylindrical shank, a lower cylindrical shank having a square drive socket, a nut, a spring between the upper cylindrical shank and the nut, wherein the spring is configured to apply a force across the upper cylindrical shank and the lower cylindrical shank, a shaft having a workpiece-engaging tip and a square drive connection engaged within the square drive socket of the lower cylindrical shank, wherein the shaft extends axially through the lower cylindrical shank, the upper cylindrical shank, the spring, and the handle with an end portion of the shaft disposed within the lumen of the handle, wherein the shaft has a plurality of thread rests on a portion of the shaft, wherein the thread rests are cut and engaged by a threading in the nut, wherein the shaft has a lumen extending across an axial length of the shaft, and wherein the shaft comprises a plastic material or a composite including plastic, wherein the upper cylindrical shank and the lower cylindrical shank engage for relative rotation, and wherein the upper cylindrical shank and the lower cylindrical shank disengage when a predetermined torque limit is exceeded, the methods further comprising aligning the torque-limiting driver relative to the workpiece by use of a guidewire delivered through the lumen of the shaft, and applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit.

DRAWINGS

The above-mentioned features of the present disclosure will become more apparent with reference to the following description taken in conjunction with the accompanying drawings wherein like reference numerals denote like elements and in which.

As shall be appreciated by those having ordinary skill in the art, the figures are not to scale, and modifications to scale within a figure or across the figures are considered within the present disclosure.

FURTHER DESCRIPTION

Figure 1:
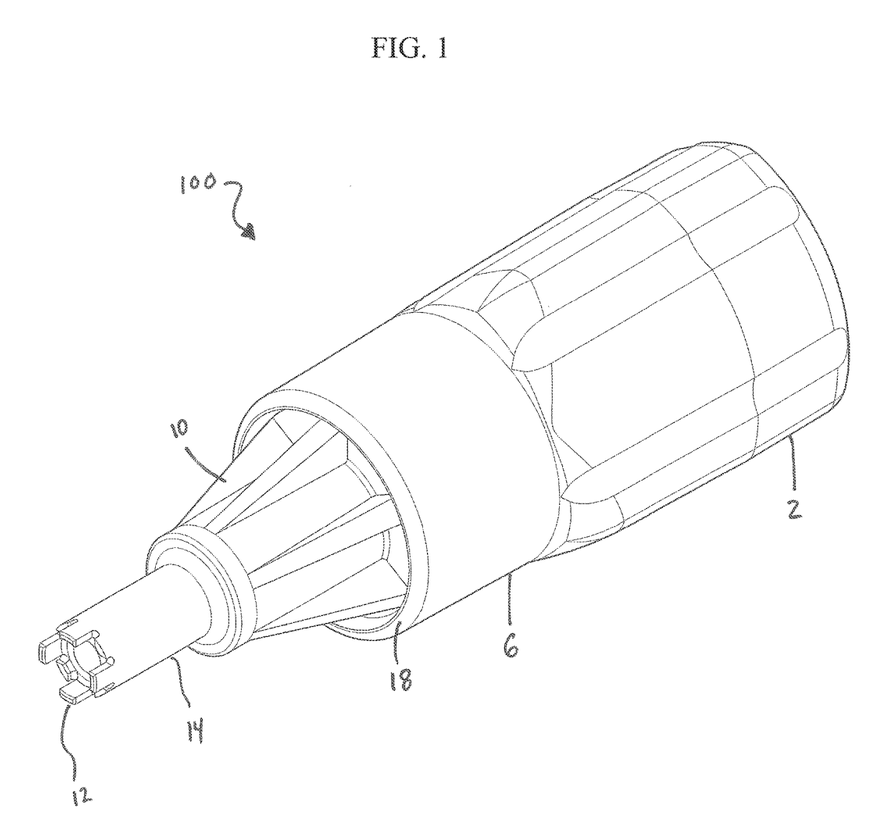
FIG. 1 shows a perspective view of some aspects of a driver.
Figure 2:
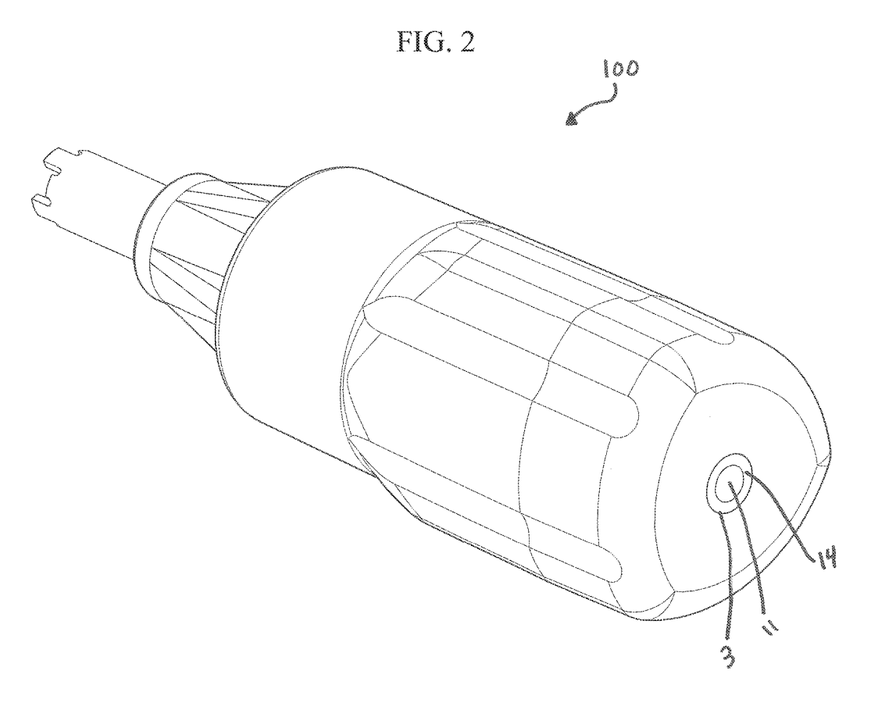
FIG. 2 shows a perspective view of some aspects of a driver.

According to one or more exemplary implementations, as shown in FIGS. 1-10, torque-limiting driver 100 may be provided. Torque-limiting driver 100 may have a generally cylindrical-shaped handle or other structure to facilitate use by a user. For example, in some implementations the handle may by "T-shaped". FIGS. 1 and 2 depict an implementation of a handle that includes an axially extending generally hollow cylindrical body 6 having a rounded triangular shape. Cap 2 covers one end of the handle. Cap 2 and body 6 may be provided with texturing, ridges, grooves, channels, or other features for a user to grip. Cylindrical end 18 terminates cylindrical body 6 toward tip 12 of shaft 14. Cap 2 may be snap-fitted to cylindrical body 6, or may be welded, adhered, or attached by any equivalent thereof. Cap 2 may include a lumen 3, in which an end portion of shaft 14 may be disposed. A lumen end opening 11 of shaft 14 may be accessible through lumen 3.

An exemplary implementation shows, at least in part, at cylindrical end 18, lower shank 700 provided, having an annularly tapering body along its length. Lower shank 700 may have a plurality of support flanges 10 that add strength while saving material. At one end, lower shank 700 tapers to drive socket 9 molded to engage drive connection 16 of shaft 14. An exemplary implementation shows, at least in part, shaft 14 provided, at the proximal end, with workpiece-engaging tip 12, adapted for engagement with an associated workpiece, such as a fastener 500 or the like. Workpiece-engaging tip 12 is shown with features adapted for driving a cannulated fastener 500, but could be a screwdriver, wrench, or any other tool arrangement. At the end opposite the tapered end, lower shank 700 has a plurality of teeth 82 arranged in a crown gear formation, with circumferential rim 31 extending radially outward and an internal axial bore to accommodate at least a portion of shaft 14 extending there through.

Figure 3:
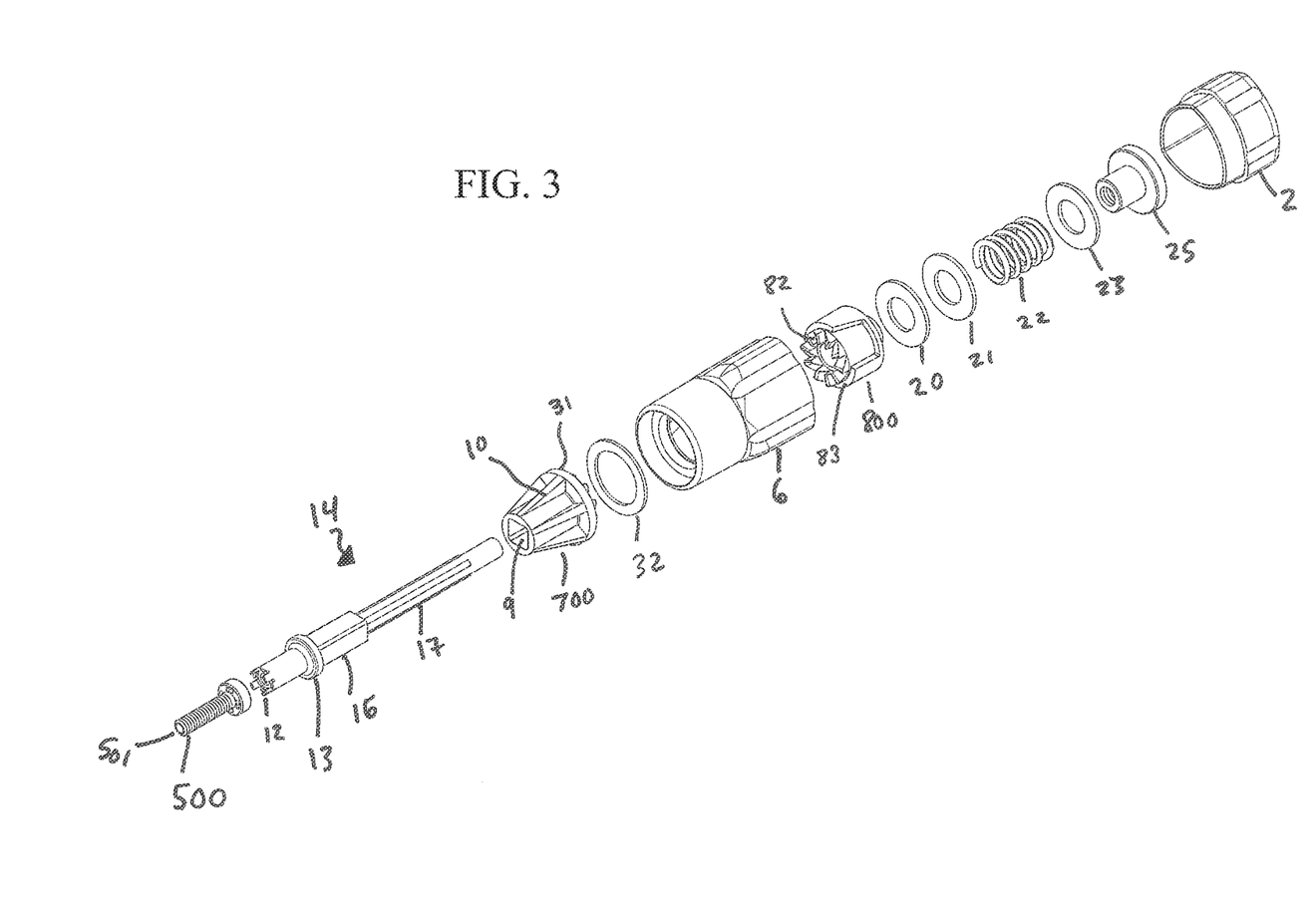
FIG. 3 shows an exploded view of some aspects of a driver.
Figure 4:
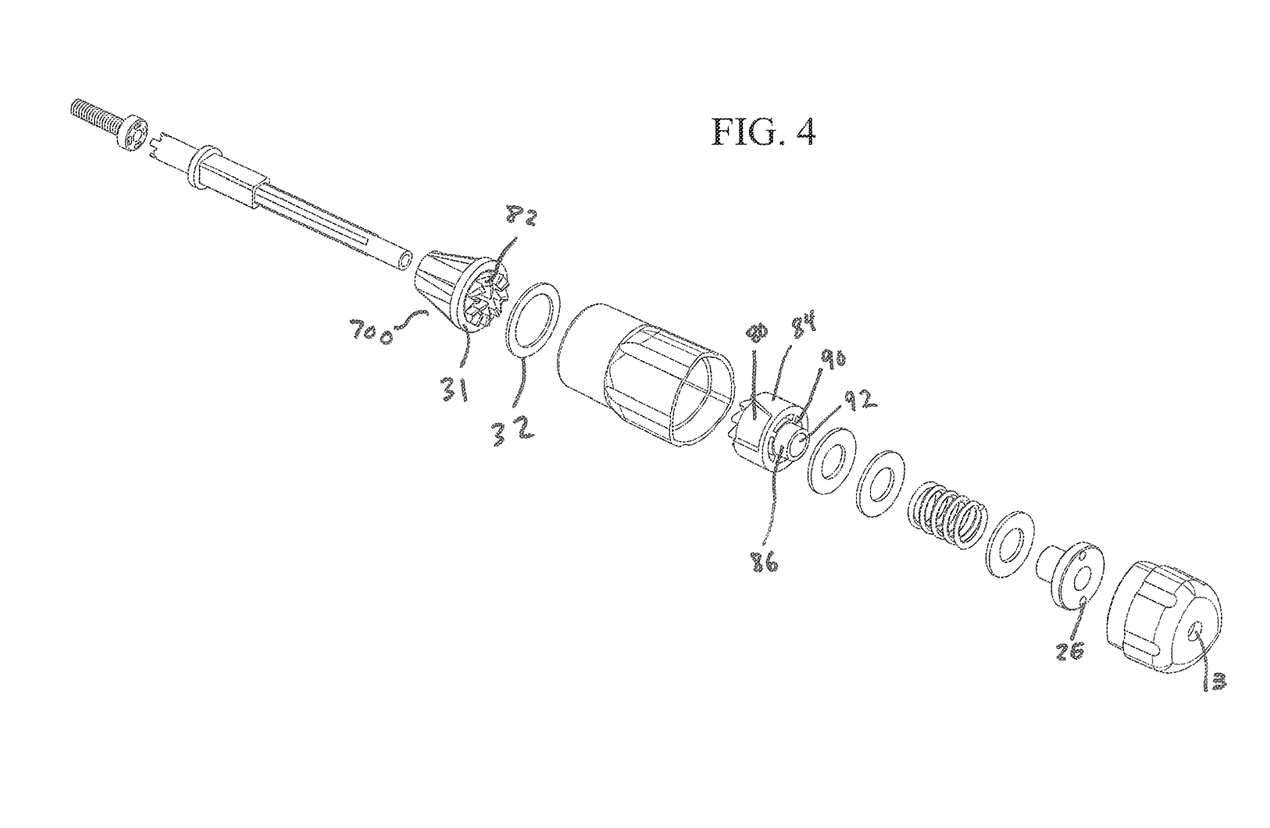
FIG. 4 shows an exploded view of some aspects of a driver.
Figure 5:
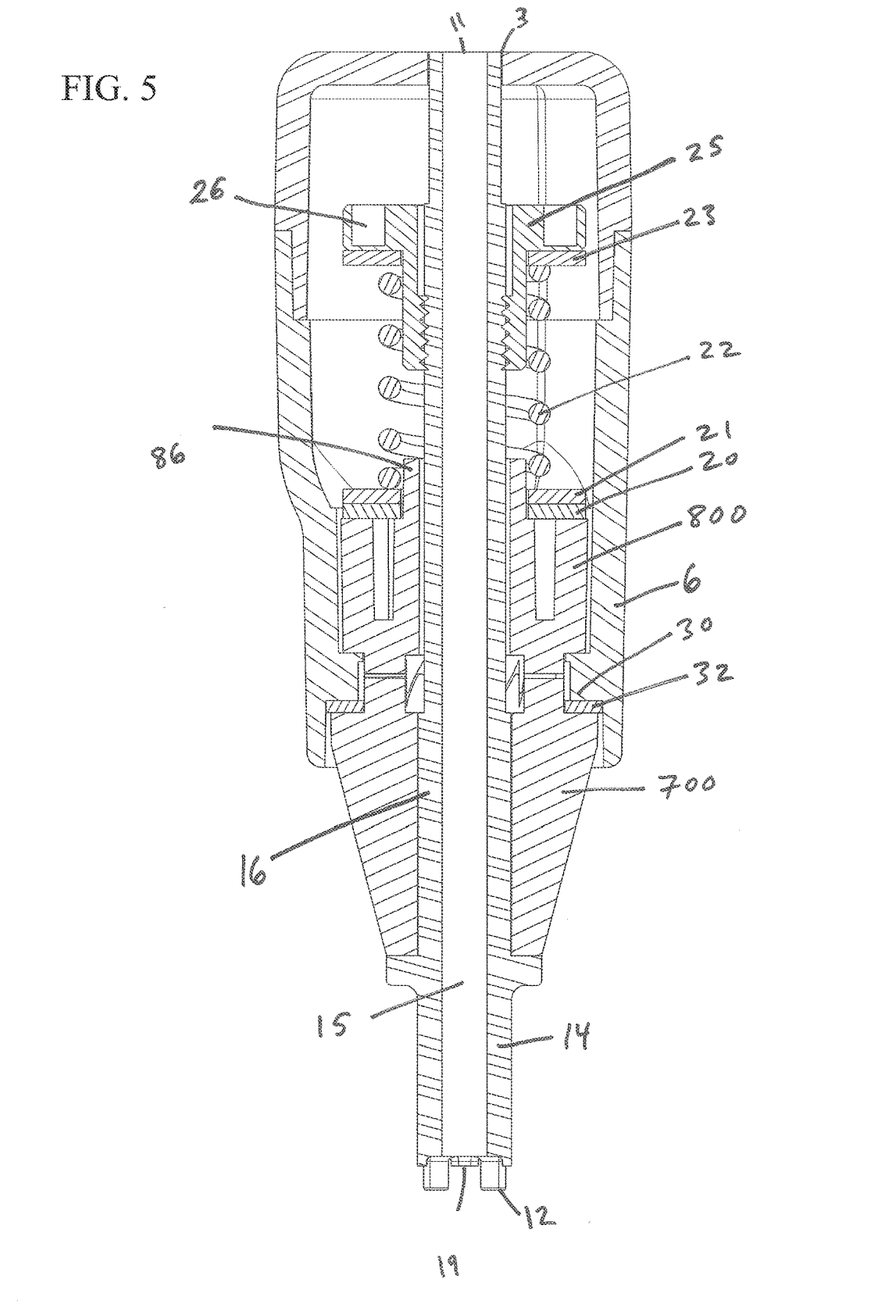
FIG. 5 shows a cross sectional view of some aspects of a driver.

According to aspects of one or more exemplary implementations, inside cylindrical body 6 a clutch assembly is disposed. The clutch assembly includes upper shank 800 for forcibly engaging lower shank 700. Upper shank 800 has a bottom face that has a plurality of teeth 82 arranged in a crown gear formation and circumferential rim 83 extending radially outward. As shown in FIGS. 3-5, upper shank 800 includes outer cylindrical shank 84 and axial bore 92 through inner shank 86. Inner shank 86 and outer shank 84 are connected via inner supports 88, leaving upper shank 800 substantially hollow with internal spaces 90 on a top face. Alternatively, upper shank 800 may be of a single contiguous piece. Inner shank 86 may extend from the top face to provide alignment and support for shaft 14, one or more washers 20 and 21, and spring 22.

According to one or more exemplary implementations, upper shank 800 includes at least one recess 80 on a side of outer shank 84. Recess 80 is provided as a cylindrical cut, relief or recess into the side of the outer shank and may be provided as a square or rectangular cut or the cut may have a slanted side or sides relative to the axis of upper shank 800, as shown in FIGS. 3 and 4.

In assembly, drive connection 16 of shaft 14 is received into drive socket 9 of lower shank 700, with collar 13 resting against the tapered end of lower shank 700 around drive socket 9. Washer 32 may be provided between circumferential rim 31 of lower shank 700 and circumferential flange 30 extending radially inward within the hollow of cylindrical body 6. Washer 32 may be of a polymer or other material having low coefficient of friction. Alternatively, circumferential rim 31 of lower shank 700 may be provided flush against circumferential flange 30 of cylindrical body 6. The opposite side of circumferential flange 30 receives circumferential rim 83 of upper shank 800, allowing teeth 82 of lower shank 700 to engage teeth 82 of upper shank 800 when a torque is applied.

Figure 6:
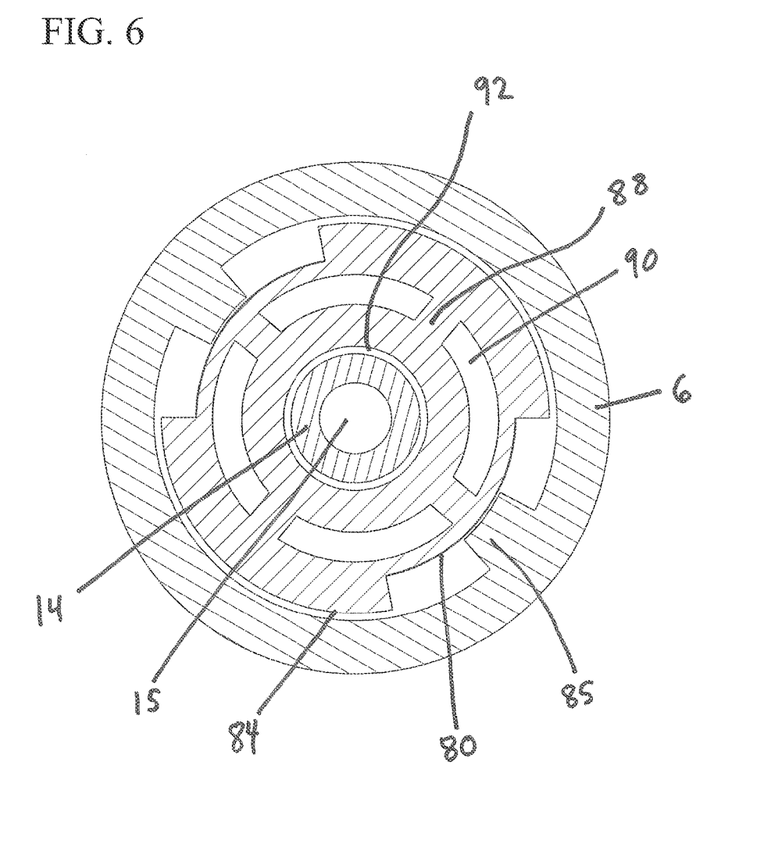
FIG. 6 shows a cross sectional view of some aspects of a driver.

According to aspects of one or more exemplary implementations, integrally formed within cylindrical body 6, protrusion 85 mates with recess 80 of upper shank 800. FIG. 6 depicts a cross-section cut-away view of driver 100, and illustrates protrusion 85 in relation with recess 80. Protrusion 85 extends inward in a radial fashion and has a length along the axis of cylindrical body 6 for relative moveable engagement within recess 80. This engagement provides a locking mechanism of shaft 14 relative to the handle via upper shank 800 when pressure is applied across lower shank 700 and upper shank 800. Recess 80 is provided circumferentially wider than protrusion 85 for allowing cylindrical body 6 and the handle to rotate in reverse a predetermined distance from a locked position without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

According to aspects of one or more exemplary implementations, force is applied across lower shank 700 and upper shank 800 via spring 22 within cylindrical body 6. Inside cylindrical body 6, shown in FIGS. 3 and 5, washer 20 and washer 21 are provided between upper shank 800 and spring 22. Washer 20 and washer 21 transfer pressure from spring 22 over the top face of upper shank 800. At an end of spring 22 opposite upper shank 800, washer 23 and nut 25 hold spring 22 in a relatively compressed state. Washer 23 may be provided between nut 25 and spring 22 to facilitate relative rotation of nut 25 and spring 22.

According to one or more exemplary implementations, shaft 14 may have a plurality of thread rests 17 at an end opposite workpiece-engaging tip 12 to engage threading within nut 25, thereby imparting pressure between the respective teeth 82 of lower shank 700 and upper shank 800. The thread rests 17 can comprise regions of additional material, relative to the remainder of the local region of the shaft, sized to be cut by the threading of nut 25 while the remainder of the local region of the shaft may slide through the nut 25 without engaging with the threading. During assembly, the threading of nut 25 can cut into the thread rests 17 on shaft 14. Nut 25 may have one or more engagement features 26 for use with an assembly drive tool to facilitate threading the nut 25 onto shaft 14. Spring 22 and nut 25 provide the proper tensioning and biasing for the clutch assembly and, generally, the nut 25 is adjustable relative to shaft 14 to provide proper tension and calibration. Thread rests 17 may be disposed on a portion of the shaft exterior extending from drive connection 16 opposite the work-piece engaging tip 12. A shaft medial segment 27 having the full thickness of the thread rests 17 may be provided proximate to drive connection 16, as shown in the shaft implementation shown in FIGS. 9 and 10. The full thickness of shaft medial segment 27 strengthens the interface with the drive connection 16. In some preferred implementations, shaft 14 is provided with three to five thread rests. In some implementations, shaft 14 is provided with four thread rests aligned with rounded corners of the square drive connection 16. The number and sizing of the thread rests can be selected to provide adequate fixation between the nut 25 and shaft 14 while avoiding providing excess thread rest material which requires more force to thread nut 25 onto the shaft 14 than the shaft 14 can withstand without failure.

According to aspects of one or more exemplary implementations, various materials may be used for the components of driver 100. According to some exemplary implementations, at least one of body 6, cap 2, shaft 14, lower shank 700, and upper shank 800 is of a plastic material or a composite including plastic. In preferred exemplary implementations, only washers 20, 21, and 23, spring 25, and nut 25 are not made from plastic material or a composite including plastic, such as a metal such as stainless steel. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. According to aspects of one or more exemplary implementations, at least one of lower shank 700 and upper shank 800 is of or includes at least one material that lubricous or otherwise reduces friction. The presence of a friction-reducing material allows geometric aspects of the engagement between lower shank 700 and upper shank 800 to govern whether teeth engage or disengage, thereby improving precision of the device.

According to aspects of one or more exemplary implementations, materials and components of drive 100 are resistant to sterilization, cleaning, and preparation operations. For example, drive 100 and parts thereof are configured to withstand sterilization by methods including radiation (e.g., gamma rays, electron beam processing), steam (e.g., autoclave), detergents, chemical (e.g., Ethylene Oxide), heat, pressure, inter alia. For example, materials for drive 100 may be selected according to resistance to one or more selected sterilization techniques.

According to aspects of one or more exemplary implementations, shaft 14 is of a rigid non-metal material. For example, shaft 14 may be of a plastic material or a composite including plastic. According to some exemplary implementations, high torque capabilities of drive 100 are, at least in part, provided by features that maintain an effective engagement between drive connection 16 of shaft 14 and drive socket 9 of lower shank 800. For example, some exemplary implementations are provided to improve the ability of drive 100 to maintain its grip on shaft 14 up to a greater range of torque.

According to aspects of one or more exemplary implementations, a single integrated shaft 14 spans the distance between workpiece-engaging tip 12 and an engagement point with nut 25. This configuration enables greater torque capabilities than a piecemeal or fragmented set of interconnected components. This reduces the number of interconnections between a source of a torque and a location to which the torque is transferred.

According to one or more exemplary implementations, shaft 14 having a drive connection 16 between opposing extensions stabilizes drive connection 16 within drive socket 9. Placement of drive connection 16 at a medial segment of shaft 14—rather than at an end thereof—facilitates a more stable engagement between drive connection 16 and drive socket 9, thereby increasing the ability of engagement to transfer high amounts of torque.

According to one or more exemplary implementations, an engagement of drive connection 16 within drive socket 9 is maintained by the connection of the integrated portion of shaft 14 that extends to nut 25. According to some exemplary implementations, both thread rests 17 and drive connection 16 are of a single integrated structure (i.e., shaft 14). A force applied by spring 22 to nut 25 is directly transferred along shaft 14 from the cut-threads interface between thread rests 17 and nut 25 to drive connection 16. This force securely maintains drive connection 16 within drive socket 9. This engagement enables transfers of greater amounts of torque from lower shank 700 (i.e., via drive socket 9) to shaft 14 (i.e., via drive connection 16).

According to aspects of some exemplary implementations, drive connection 16 and drive socket 9 have complementary geometries. One or more of a variety of configurations may be provided for engaging drive connection 16 within drive socket 9. For example drives and associated connections may include triangular, square, hexagonal, rectangular, etc. According to aspects of one or more exemplary implementations, a substantially square drive connection 16 and drive socket 9 provide high torque transfer capabilities. Out of a variety of drive types, experimental results demonstrated that square drives and connections were among the most successful at transferring high torque without failure. Drive connection 16 and drive socket 9 may have rounded corners and edges to reduce or distribute stress risers.

In some exemplary implementations, rounded or truncated corners may be provided between the walls of the square cross section drive connection 16 to the drive socket 9 of lower shank 700 in order to more evenly distribute the force applied thereto and substantially reduce deformation, bending, breaking, and/or cracking of the lower shank 700 or shaft 14 at high load. Drive connection 16 is less likely to "strip", deform, or spin in the drive socket 16 than shafts incorporating drive connections with other geometric cross-sections. The corners may be provided with a truncation diameter to distribute the load caused by turning shaft 14 at a predetermined torque over a predetermined number of rotations without cracking the shaft 14 or plastic material of lower shank 700 that surrounds the drive socket 9 to a point of failure. The optimal range of dimensions to achieve even (as in even load) repetitive rotations can be selected to correspond to the torque requirements of a particular driver.

Figure 11:
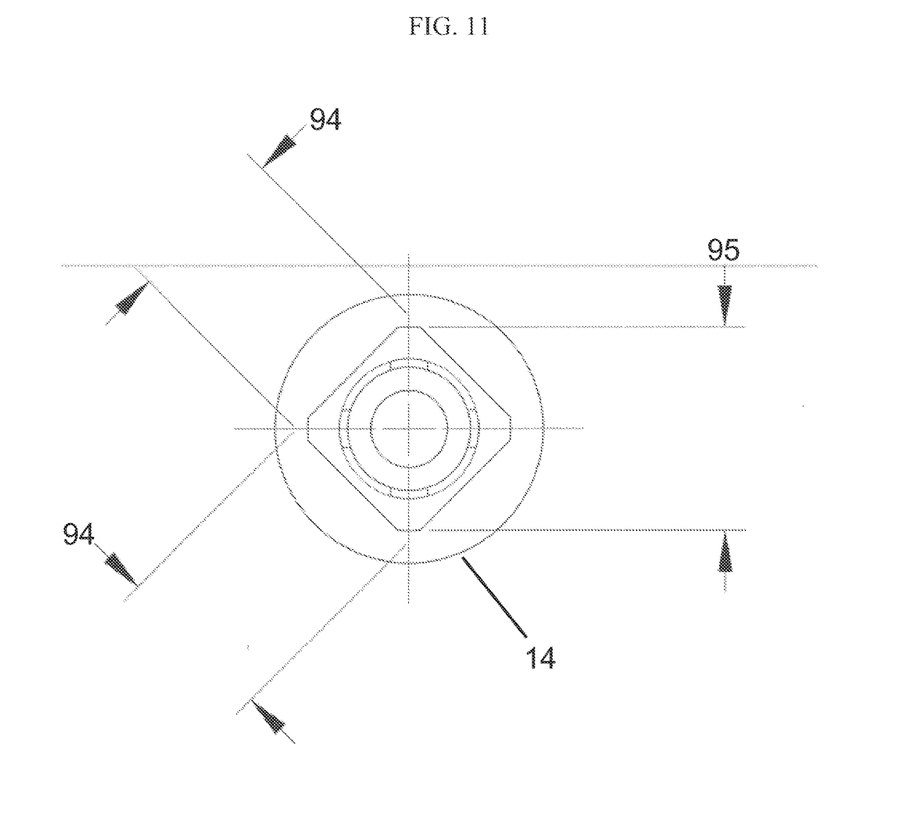
FIG. 11 shows an end view of some aspects of a shaft.

In some implementations, a square geometry is provided for each of the drive connection 16 and the drive socket 9, with truncated corners. As depicted in FIG. 11, shaft 14 can be provided with a drive connection 16 having a square geometry with four substantially planar walls with truncated corners interposed between the substantially planar walls, with nominal side lengths 94 and truncated diameter distance 95. An untruncated diameter distance would be equal to nominal side length 94 times the square root of two, if sharp corners were provided at the intersections of the four sides of the drive connection 16 instead of truncated corners. In some implementations a truncated diameter distance 95 of about 1% to about 20% less than an untruncated diameter distance may be provided. In some implementations a truncated diameter distance 95 of about 5% to about 15% less than an untruncated diameter distance may be provided. In some implementations a truncated diameter distance 95 of about 8% to about 12% less than an untruncated diameter distance may be provided. In some preferred implementations a truncated diameter distance 95 of about 10% less than an untruncated diameter distance may be provided. In some implementations, a nominal side length 94 of about 0.194 inches and a truncated diameter distance 95 of about 0.247 inches can be provided. A corresponding drive socket 9 should be provided with slightly larger dimensions to account for tolerances in production and allow drive connection 16 to slide into drive socket 9. In some implementations, for the drive socket 9 each of the nominal side length 94 and truncated diameter distance 95 may be provided from about 0.002 to about 0.005 inches larger than in the profile of the corresponding drive connection 16. The difference in size should not be so large as to allow for "play" or a loose connection between the drive socket 9 and drive connection 16. In some implementations a nominal side length 94 of about 0.194 inches for the drive connection 16 and of about 0.197 inches for the drive socket, and a truncated diameter distance 95 of about 0.247 inches for the drive connection 16 and of about 0.250 inches for the drive socket can be provided.

According to aspects of one or more exemplary implementations, driver 100 capable of transferring higher torque may be provided with spring 22 having a greater spring constant (i.e., force constant) or otherwise be calibrated with spring 22 exerting greater forces in an initial (rest) state. A more robust spring 22 may washer 20 and washer 21 may both be provided where spring 22 may have a tendency to grip relative to washer 21. A more robust spring 22 increases the probability of a friction grip relative to washer 21. Provision of additional washer 20 preserves at least one free-spinning structure between spring 22 and upper shank 800.

Figure 8:
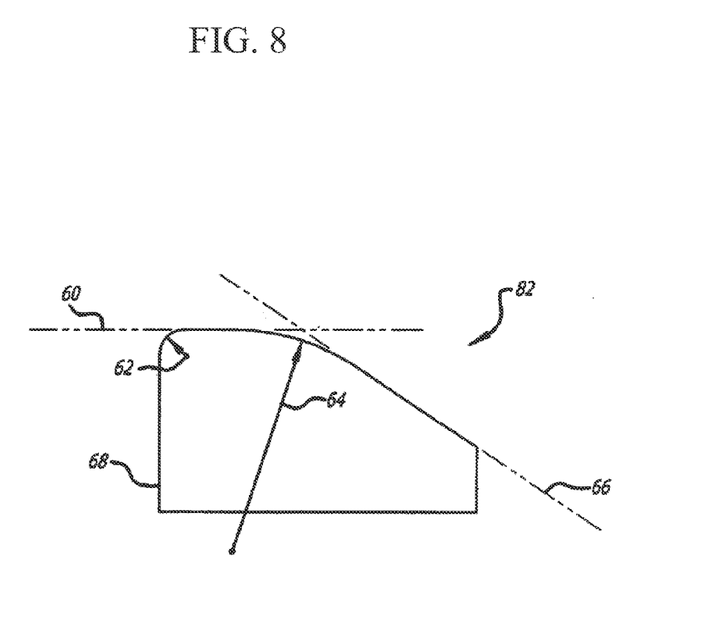
FIG. 8 shows a profile view of some aspects of a tooth from a clutch assembly.
Figure 9:
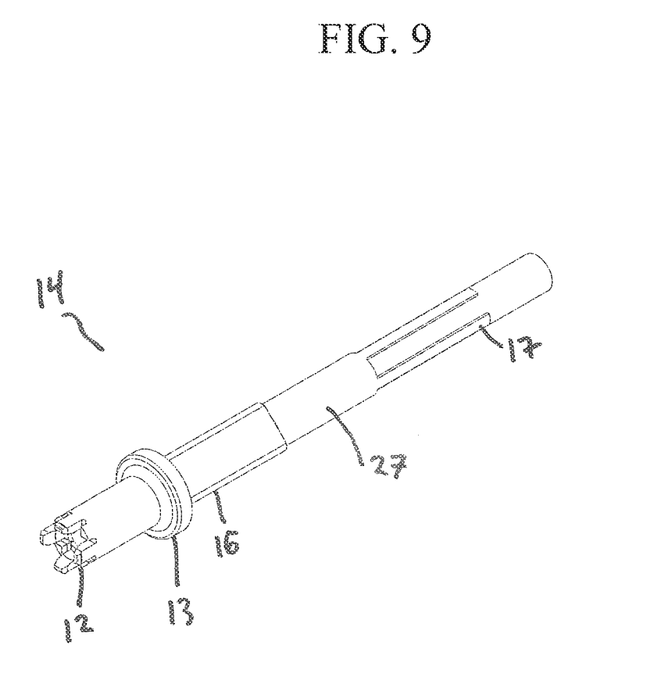
FIG. 9 shows a perspective view of some aspects of a shaft.
Figure 10:
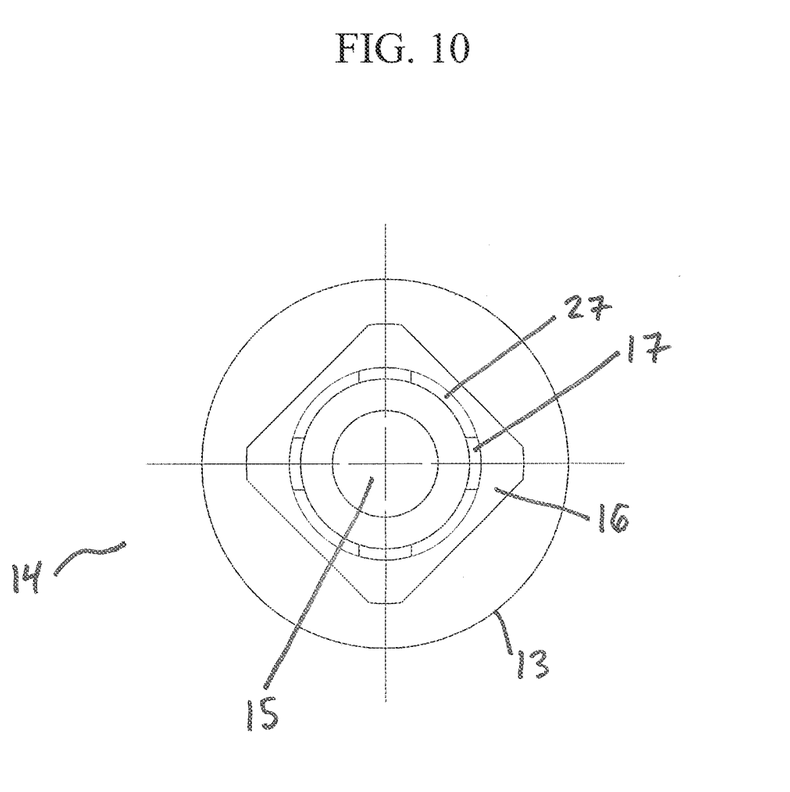
FIG. 10 shows an end view of some aspects of a shaft.

According to aspects of one or more exemplary implementations, nut 25 may provide a lower portion having outer diameter substantially equal to an inner diameter of spring 22. The lower portion of nut 25 may extend axially through at least a portion of spring 22. The lower portion of nut 25 may maintain relative axial alignment between nut 25 and spring 22 by limiting travel of spring 22 other than by compression thereof According to aspects of one or more exemplary implementations, the plurality of teeth 82 are formed on the top face of lower shank 700 and the bottom face of upper shank 800 to forcibly engage to impart torque from the handle to the workpiece when a torque is applied. Referring to FIG. 8, tooth 82 has inclined face 66 that smoothly transitions to substantially flat peak 60, via first radius of curvature 64. Substantially flat peak 60 subsequently transitions smoothly, via second radius of curvature 62, to vertical face 68 that is substantially parallel to the axis of lower shank 700 and upper shank 800. First radius of curvature 64 is typically much larger than second radius of curvature 62.

Experimental results have shown that a tooth having an inclined face that smoothly transitions to a substantially flat face is capable of imparting a substantial increase in torque to a fastener. In one experiment, a ten-fold increase in torque was observed. This increase in torque is due to the frictional forces associated with the smoothly transitioning curve of inclined face 66 of teeth 82.

In a simplified example, when two uniform inclines are frictionally engaged, only one static force, having a single coefficient of static force, is acting against the relative movement of the two inclines. However, when the two inclines are not uniform, more than one coefficient of static force can be observed, thus resulting in a higher disinclination to movement.

Figure 7:
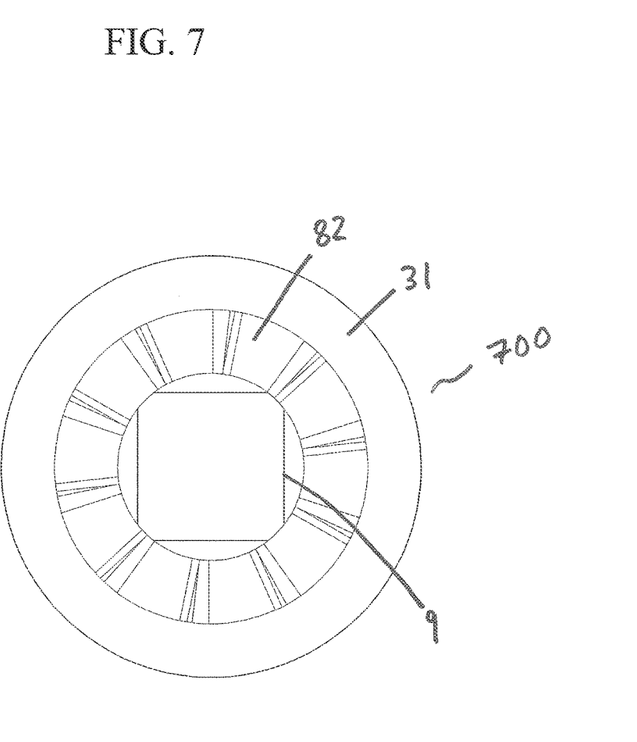
FIG. 7 shows an end view of some aspects of a lower shank.

According to aspects of one or more exemplary implementations, teeth 82 are circumferentially spaced in a crown gear formation of the top face and bottom face of lower shank 700 and upper shank 800, respectively. Teeth 82 are preferably configured in a spiral formation, as shown in FIGS. 3, 4, and 7. Each face of lower shank 700 and upper shank 800 has an inner radius and an outer radius and teeth 82 spiral around the inner radius resulting in a larger tooth detail when viewing the tooth from the outer radius relative to the tooth detail when viewing the tooth from the inner radius. The spiral configuration of teeth 82 can also be defined as having a longer inclined face 66 at the edge of the tooth on or near the outer radius relative to inclined face 66 at the edge of the tooth on or near the inner radius of lower shank 700 and upper shank 800. Results have shown that teeth arranged in said spiral configuration provide an increased reliability and/or precision in torque consistency when compared to non-spiral counterparts.

Substantially flat peaks 60 of teeth 82 may be as wide at the inner radius as they are at the outer radius. Alternatively, substantially flat peaks 60 may be wider at the outer radius and taper toward the inner radius.

Vertical faces 68 of teeth 82 of lower shank 700 and upper shank 800 respectively engage when a torque is applied to prevent relative rotation of lower shank 700 and upper shank 800 in one direction. Inclined faces 66 engage to accommodate relative rotation of lower shank 700 and upper shank 800 in an opposite direction.

According to aspects of one or more exemplary implementations, the extent to which thread rests 17 of shaft 14 are threaded into nut 25 controls the amount of compression or preload on spring 22 which, subsequently, controls the limiting torque required to effect relative rotation of lower shank 700 and upper shank 800. If shaft 14 is more deeply threaded into nut 25, then a higher torque will be required to disengage teeth 82 of lower shank 700 and upper shank 800. If shaft 14 is less deeply threaded into nut 25, then a lower torque will be required to disengage teeth 82 of lower shank 700 and upper shank 800. Accordingly, a predetermined torque limit is selectively programmable. The predetermined torque limit may correspond to a predefined threshold of a workpiece (e.g., a fastener) having a desired level of torque-based installation not to be exceeded.

According to one or more exemplary implementations, when driver 100 is rotated in one direction under an applied torque, shaft 14 will rotate with cylindrical body 6 and handle until a predetermined torque limit is reached. When the predetermined torque limit is reached or exceeded by the applied torque, a biasing force exerted by spring 22 will be overcome, allowing inclined face 66 of upper shank 800 to slide up a respective inclined face 66 of lower shank 700, subsequently snapping each tooth 82 of lower shank 700 into engagement behind a next tooth 82 of upper shank 800. This snapping sound is typically an audible indication to a user that a predetermined torque limit has been reached or exceeded.

When a force beyond the predetermined torque limit is achieved, teeth 82 of lower shank 700 and upper shank 800 will continue to disengage, resulting in rotation of the handle with no further rotation of workpiece-engaging tip 12. Thus, the handle will continue to rotate, disengaging teeth 82 with every rotational movement that will not impart continued force beyond a predefined threshold to the fastener.

According to one or more exemplary implementations, when driver 100 is rotated in the opposite direction, the handle rotates in reverse a predetermined distance from a locked position without subsequent reverse rotation of workpiece-engaging tip 12. However, when protrusion 85 travels the provided distance within recess 80 and locks against the opposite end of recess 80, driver 100 will operate as a standard driver with no torque-limiting feature since engaging vertical face 68 will force relative rotation of lower shank 700 and upper shank 800 in the opposite direction without any torque-limiting feature.

According to aspects of one or more exemplary implementations, the disposable torque-limiting driver of the present disclosure is capable of imparting torques of up to about 40 inch-ounces. For example, the torque output range may be selected between about 16 inch-ounces and about 40 inch-ounces. Typically, the torque requirement is different for different operations and for different implants. For example, applications may include those in the field of orthopedic surgery, construction and emplacement of implants, etc. Therefore, in some instances, the predetermined torque limit may be at least about 1 inch-ounce. In other instances, the predetermined torque limit may be between about 5 inch-ounces and about 40 inch-ounces, depending on an implant's specifications. In other instances, the predetermined torque limit may be between about 16 inch-ounces and about 40 inch-ounces, depending on an implant's specifications.

According to one or more exemplary implementations, as shown in FIG. 5, shaft 14 may be cannulated to include lumen 15. Lumen 15 may extend along the entire length of shaft 14, with a lumen end opening 11 and a lumen tip opening 19 (at workpiece-engaging tip 12), said openings in some instances being in fluid communicating with each other. Body 6 may provide access to lumen 15, such as via aperture 3 of cap 2 that exposes lumen end opening 11. According to some exemplary implementations, lumen 15 may accommodate one or more devices or materials for use in tandem with the torque capabilities of driver 100. According to some exemplary implementations, a guidewire to aide in driver alignment may be provided through lumen 15. According to some exemplary implementations, lumen 15 may accommodate a tube delivering a biologic material to be dispensed before, during, or after torque is applied. For example, the biologic material could be an adhesive to assist in locking or staking a fastener to which torque was applied. By further example, the biologic material may assist in stimulation of bone growth (i.e., growth stimulant). Lumen 15 may accommodate one or more devices. Such devices may include a sound-emitting device (e.g., ultrasound, etc.), a radiation-emitting device (e.g., light, laser, LED, etc.), a drilling device, a cutting device, an ablation device, a curing device, a retrieval device, an aspiration device, a suction device, an irrigation device, a gasification device, a cooling device, a heating device, an optical device (e.g., scope for viewing, etc.), inter alia. In some implementations, driver 100 may be used in conjunction with a fastener 500 that includes a lumen 501. Lumen 501 may interface with lumen tip opening 19 to provide a continuation of lumen 15 through the fastener.

In some instances, a torque-limiting driver, such as driver 100, may be prepackaged with an implant provided for one-time use. Such a methodology matches the driver that will impart a required amount of torque with the implant.

In some implementations, the driver 100 may be disposable. In some implementations, the drive connection 16 and drive socket 9 having square geometry with truncated corners and the parameters of shaft 14 provide a range of use over a limited and predetermined number of torque-limit actuations for a particular predetermined torque limit before the drive socket 9, the shaft 14 at one or more points within or between drive connection 16 and thread rests 17, or a combination of two or more of those elements together, fails structurally. These failures are intentionally designed to occur after a limited number of torque-limit actuations before the performance of driver 100 begins to vary from the predetermined torque limit. This provides the benefits of ensuring performance within specification for a procedure and ensuring that once the driver has been used it is discarded in order to mitigate the improper repeat use of driver 100 across multiple procedures, which can increase the chances of cross-patient contamination. The term "torque-limit actuation" refers to when the predetermined torque limit is reached or exceeded by the applied torque and the upper cylindrical shank and the lower cylindrical shank disengage. In some implementations the predetermined number of torque-limit actuations is limited to no more than about two actuations. In further implementations, the predetermined number of torque-limit actuations is limited to no more than about five actuations, no more than about ten actuations, no more than about twenty actuations, no more than about forty actuations, or no more than about sixty actuations.

In other instances, the driver 100 may be reusable. Shaft 14 may be interchangeably fixed relative to the tapered end of lower shank 700 for the accommodation of multiple workpiece-engaging tips 12. It is also to be appreciated that the handle of the driver is not limited to rounded triangular shape and may be provided in any other suitable configuration.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:
1. A torque-limiting driver comprising:
a body having a handle comprising a first lumen;
an upper cylindrical shank;
a lower cylindrical shank having a square drive socket;
a nut;

a spring between the upper cylindrical shank and the nut, wherein the spring is configured to apply a force across the upper cylindrical shank and the lower cylindrical shank;

a shaft having a workpiece-engaging tip and a square drive connection engaged within the square drive socket of the lower cylindrical shank, the shaft extending axially through the lower cylindrical shank, the upper cylindrical shank, the spring, and the handle with an end portion of the shaft disposed within the first lumen, the shaft having a plurality of thread rests on a portion of the shaft, the thread rests cut and engaged by a threading in the nut, the shaft having a second lumen extending across an axial length of the shaft, and the shaft comprising a plastic material or a composite including plastic; and, wherein the upper cylindrical shank and the lower cylindrical shank engage for relative rotation, and wherein the upper cylindrical shank and the lower cylindrical shank disengage when a predetermined torque limit is exceeded;

wherein the second lumen extends along the entire length of the shaft, with the second lumen having a lumen tip opening disposed at the workpiece-engaging tip and a second lumen end opening disposed at the opposite end of the shaft at the end portion.

2. The torque-limiting driver of claim 1, wherein the second lumen encloses a tube advanceable within the second lumen.

3. The torque-limiting driver of claim 2, wherein the tube is configured to deliver a biologic material.

4. The torque-limiting driver of claim 3, wherein the biologic material is an adhesive.

5. The torque-limiting driver of claim 3, wherein the biologic material is a growth stimulant.

6. The torque-limiting driver of claim 1, wherein the second lumen encloses a guidewire advanceable within the second lumen.

7. The torque-limiting driver of claim 1, wherein the plurality of thread rests consist essentially of four thread rests aligned with the corners of the square drive connection.

8. The torque-limiting driver of claim 1, wherein the shaft includes a medial segment disposed between the thread rests and the square drive connection having the full thickness of the thread rests.

9. The torque-limiting driver of claim 1, wherein a force provided by the spring securely maintains the square drive connection of the shaft engaged within the square drive socket of the lower cylindrical shank.

10. The torque-limiting driver of claim 1, wherein the nut includes a lower portion having an outer diameter substantially equal to an inner diameter of the spring and extending axially through at least a portion of the spring.

11. The torque-limiting driver of claim 1, further comprising at least two washers between the spring and the upper cylindrical shank.

12. The torque-limiting driver of claim 1, further comprising a washer between the lower cylindrical shank and the body.

13. The torque-limiting driver of claim 1, further comprising a washer between the spring and the nut.

14. The torque-limiting driver of claim 1, wherein the upper cylindrical shank and the lower cylindrical shank each have a plurality of teeth and an axial bore, the teeth having a vertical face, an inclined face and a substantially flat peak, wherein the inclined face is defined by a first radius of curvature that transitions to the substantially flat peak and wherein the teeth spiral around the axial bore.

15. The torque-limiting driver of claim 14, wherein the vertical face terminates in a second radius of curvature that transitions to the substantially flat peak and wherein the second radius of curvature is smaller than the first radius of curvature.

16. The torque-limiting driver of claim 14, wherein the substantially flat surface is wider at the outer radius than at the inner radius and wherein the substantially flat surface is perpendicular to the axis of the upper and lower shank.

17. The torque-limiting driver of claim 15, wherein the transition from the first radius of curvature and second radius of curvature to the substantially flat peak is smooth.

18. The torque-limiting driver of claim 1, wherein the predetermined torque limit is at least 1 inch-ounce.

19. The torque-limiting driver of claim 1, wherein the predetermined torque limit is between about 16 inch-ounces and about 40 inch-ounces.

20. The torque-limiting driver of claim 19, wherein the torque-limiting driver is capable of functioning within the predetermined torque limit for a predetermined number of torque-limit actuations before the drive socket, the shaft at one or more points within or between drive connection and thread rests, or a combination of two or more of those elements together, fails structurally.

21. The torque-limiting driver of claim 20, wherein the predetermined number of torque-limit actuations is no more than about ten.

22. The torque-limiting driver of claim 20, wherein the predetermined number of torque-limit actuations is no more than about twenty.

23. The torque-limiting driver of claim 20, wherein the predetermined number of torque-limit actuations is no more than about forty.

24. The torque-limiting driver of claim 1, wherein the square drive connection and square drive socket are each provided with a square geometry with four substantially planar walls with truncated corners interposed between the substantially planar walls.

25. The torque-limiting driver of claim 24, wherein each of the four substantially planar walls has a nominal side length and each opposing pair of truncated corners are separated by a truncated diameter distance, wherein the truncated diameter distance is between about 1% and about 20% less than an untruncated diameter distance equal to the nominal side length times the square root of two.

26. The torque-limiting driver of claim 25, wherein the truncated diameter distance is between about 5% and about 15% less than the untruncated diameter distance.

27. The torque-limiting driver of claim 25, wherein the truncated diameter distance is between about 8% and about 12% less than the untruncated diameter distance.

28. The torque-limiting driver of claim 25, wherein the truncated diameter distance is about 10% less than the untruncated diameter distance.

29. The torque-limiting driver of claim 1, wherein the lumen tip opening and the second lumen end opening are in fluid communication with each other.

\* \* \* \* \*